(12) United States Patent
Brottier et al.

(10) Patent No.: US 12,279,815 B2
(45) Date of Patent: Apr. 22, 2025

(54) MULTIPURPOSE OPHTHALMOLOGICAL MEASURING DEVICE

(71) Applicant: E-SWIN DEVELOPPEMENT, Houdan (FR)

(72) Inventors: Yves-Vincent Brottier, Adainville (FR); Arnaud Obin, Paray-Douaville (FR); Nelson Perrin, Sainte-Mesme (FR)

(73) Assignee: E-SWIN DEVELOPPEMENT, Houdan (FR)

( * ) Notice: Subject to any disclaimer, the term of this patent is extended or adjusted under 35 U.S.C. 154(b) by 544 days.

(21) Appl. No.: 17/753,604

(22) PCT Filed: Sep. 11, 2020

(86) PCT No.: PCT/FR2020/051578
§ 371 (c)(1),
(2) Date: Mar. 9, 2022

(87) PCT Pub. No.: WO2021/048509
PCT Pub. Date: Mar. 18, 2021

(65) Prior Publication Data
US 2022/0313074 A1 Oct. 6, 2022

(30) Foreign Application Priority Data
Sep. 13, 2019 (FR) ...................... 1910131

(51) Int. Cl.
*A61B 3/00* (2006.01)
*A61B 3/10* (2006.01)
(Continued)

(52) U.S. Cl.
CPC .......... *A61B 3/0008* (2013.01); *A61B 3/1005* (2013.01); *A61B 3/101* (2013.01); *A61B 3/145* (2013.01); *A61B 3/185* (2013.01)

(58) Field of Classification Search
CPC ..... A61B 3/0008; A61B 3/1005; A61B 3/101; A61B 3/145; A61B 3/185; A61B 3/0083;
(Continued)

(56) References Cited

U.S. PATENT DOCUMENTS 6,150,666 A * 11/2000 Engelhardt .......... G02B 27/143
250/559.22
2003/0071987 A1* 4/2003 Matsumura ............ G01B 11/24
356/124

(Continued)

FOREIGN PATENT DOCUMENTS

AT 317410 8/1974
EP 0815789 1/1998
(Continued)

OTHER PUBLICATIONS

International search report for PCT/FR2020/051578 dated Dec. 14, 2020.

*Primary Examiner* — Mohammed A Hasan
(74) *Attorney, Agent, or Firm* — Perman & Green, LLP

(57) ABSTRACT

An ophthalmological measuring device including an ocular measuring unit including a front face provided with a frame encircling a translucent plate the size and curvature of which are suitable for covering the ocular field of said patient, a device for providing uniform backlighting of the translucent plate, located behind the translucent plate, at least one camera equipped with an objective placed in line with a hole in the translucent plate, one or more point light sources in apertures on the edges of the translucent plate, for illuminating the eyes of the patient, and means for fastening one or more additional ophthalmological measuring devices to the translucent plate.

19 Claims, 3 Drawing Sheets

(51) Int. Cl.
*A61B 3/14* (2006.01)
*A61B 3/18* (2006.01)

(58) Field of Classification Search
CPC .. A61B 3/024; A61B 3/13; A61B 3/18; A61B 3/0091
USPC .......................................................... 351/221
See application file for complete search history.

(56) References Cited

U.S. PATENT DOCUMENTS

| | | | | |
|---|---|---|---|---|
| 2004/0013423 | A1* | 1/2004 | Wells ..................... | G03B 13/08 |
| | | | | 396/296 |
| 2005/0231686 | A1* | 10/2005 | Rathjen .................... | A61B 3/16 |
| | | | | 351/205 |
| 2012/0274897 | A1* | 11/2012 | Narasimha-Iyer ..... | A61B 3/113 |
| | | | | 351/205 |
| 2017/0285337 | A1 | 10/2017 | Wilson et al. | |
| 2019/0357767 | A1* | 11/2019 | Nekrassov ............... | A61B 3/14 |

FOREIGN PATENT DOCUMENTS

| | | |
|---|---|---|
| EP | 1854400 | 11/2007 |
| JP | 03173527 | 7/1991 |
| RU | 179414 | 5/2018 |
| RU | 2669228 | 10/2018 |
| WO | 2015087786 | 6/2015 |

* cited by examiner

MULTIPURPOSE OPHTHALMOLOGICAL MEASURING DEVICE

CROSS-REFERENCE TO RELATED APPLICATIONS

This application is a National Stage of International Application No. PCT/FR2020/051578, having an International Filing Date of 11 Sep. 2020, which designated the United States of America, and which International Application was published under PCT Article 21(2) as WO Publication No. 2021/048509 A1, which claims priority from and the benefit of French Patent Application No. 1910131, filed on 13 Sep. 2019, the disclosures of which are incorporated herein by reference in their entireties.

BACKGROUND

Field

The invention relates to the field of ophthalmological devices for performing measurements on the eyes of patients.

BRIEF DESCRIPTION OF RELATED DEVELOPMENTS

Ophthalmological devices with which patients have to look at a particular point while a practitioner observes their eyes are known.

To date, these ophthalmological devices do not provide any great versatility.

SUMMARY

The present application relates to an ophthalmological measuring device which is versatile in the sense that it groups together several types of measuring devices and can be used in several configurations.

More precisely, the present application proposes an ophthalmological measuring device which has an ocular measurement housing comprising a front face provided with a frame surrounding a translucent plate of a size and curvature suitable for covering the ocular field of said patient, a device for lighting the translucent plate from behind the translucent plate, at least one camera provided with a lens placed in line with a hole in the translucent plate, one or more point light sources in openings on the translucent plate in order to illuminate the eyes of the patient, and means for fixing one or more complementary ophthalmological measuring devices received on the translucent plate.

The present disclosure thus proposes a compact device provided with several measuring means for carrying out several different examinations.

Preferably, the device for lighting the translucent plate from behind the translucent plate comprises an integration box diffusing the light from a white and/or near infrared light source.

The lighting is thus homogeneous at the level of the translucent plate.

According to an advantageous embodiment, the point light sources comprise blue light emitting diodes.

Such diodes are suitable for examinations under fluorescein.

According to a particular embodiment, the ophthalmological measuring device of the application is equipped with a complementary examination device consisting of a translucent frame carrying a test pattern provided with at least one hole aligned with a said camera lens, said frame comprising fixing means complementing the fixing means of said ophthalmological measuring device.

According to a first embodiment, the housing comprises means for fixing to a helmet positioned on the head of a patient. The fixing means can in particular be arranged under a second upper cover of the device and are intended to cooperate with complementary fixing means of the helmet.

According to a second alternative or complementary embodiment, the housing comprises means for fixing to an ophthalmological table frame on which the patient leans.

The means for fixing the device to said ophthalmological table frame can comprise an upper cover provided with seats for receiving endings of uprights of the frame.

According to an advantageous embodiment, the housing comprises at least one electronic board with microprocessor comprising means for controlling the lighting means and the cameras, means for acquiring video or photographic data coming from the cameras, and calculation means comprising one or more measurement computer programs comprising computer processing of the acquired video or photographic data, a touch screen integrated into the device in order to control the device according to the measurement computer program(s) and to display results of ophthalmic measurements from the computer processing carried out by the electronic board.

The device of the present disclosure thus constitutes an autonomous and multipurpose examination apparatus.

The present disclosure further proposes, according to a first embodiment, an ophthalmological measuring assembly comprising an ophthalmological measuring helmet, positioned on the head of a patient, and an ophthalmological measuring device fixed to the helmet.

The present disclosure also proposes, according to a second embodiment, an ophthalmological measuring assembly comprising an ophthalmological table frame and an ophthalmological measuring device fixed to said frame.

The measuring device of the present disclosure can thus be used in two configurations by changing an interface plate.

BRIEF DESCRIPTION OF THE DRAWINGS

Other features, details and advantages of the present disclosure will become clear from reading the following detailed description and from analyzing the accompanying drawings, in which.

DETAILED DESCRIPTION

The drawings and the description below contain, for the most part, elements of certain character. They may therefore not only serve for better understanding the present disclosure, but also contribute to its definition, where appropriate.

Figure 1:
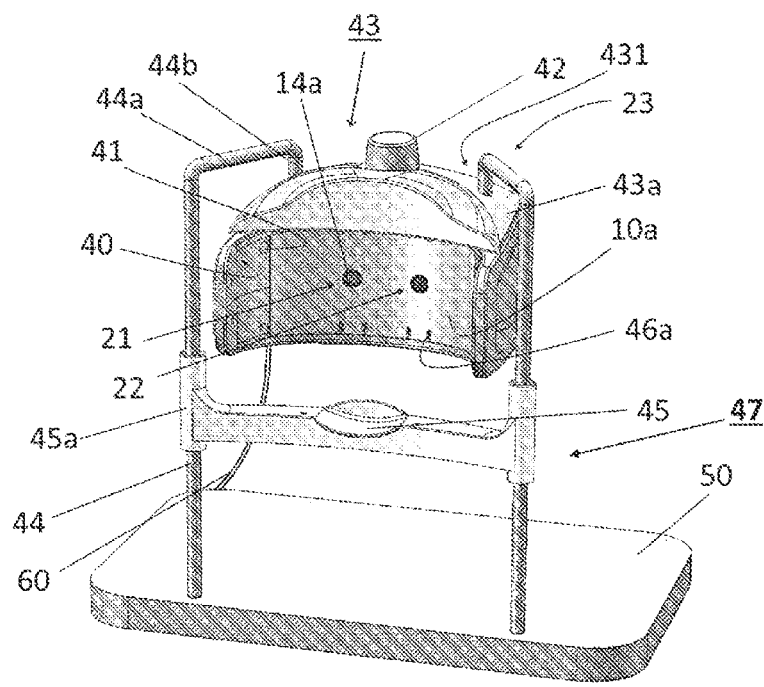
FIG. 1 shows a perspective view of a first embodiment of an ophthalmological measuring assembly of the present disclosure.

Reference is now made to FIG. 1. In this figure, corresponding to a first embodiment of an ophthalmological measuring assembly of the present disclosure, an ophthalmological measuring device 43 is mounted on an ophthalmological table frame 47.

The frame comprises uprights 44, a chin support 45, and a support plate 50. The uprights 44 have their lower ends fixed on the support plate 50, a vertical part receiving arms 45a for fixing the chin support 45, and a curved upper part 44a provided with endings 44b facing downward and fitting into seats 431 on an upper cover 43a of the ophthalmological measuring device, for example screwed onto the housing 43.

The fixing of the uprights on the device can be achieved by various traditional means such as screws securing the endings of the uprights in the seats of said cover.

Figure 2:
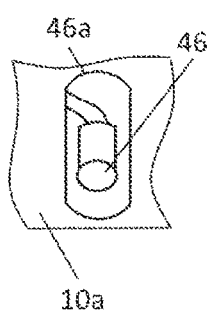
FIG. 2 shows a detail of FIG. 1.

The ophthalmological measuring device comprises a housing 43 which will contain means for performing several types of ophthalmological measurements. These means consist in particular of devices for lighting the eyes. The device comprises a diffuse lighting means consisting of a curved translucent plate 10a behind which there is a homogeneous backlighting device 23 such as an integration box shown schematically in FIG. 3, enclosed behind the housing 43, and point lighting means 46 shown in FIG. 2 and distributed here over an upper edge and a lower edge of the translucent plate in openings 46a.

The backlighting device can comprise one or more LEDs 23a in white light, near infrared light or other wavelengths, depending on the ophthalmological examinations that are to be carried out.

The point lighting means are in particular light-emitting diodes (LEDs) and comprise blue LEDs suitable for examinations with fluorescein.

The lighting means are switched on and off independently by means of an electronic board 24 in the housing.

Another important feature of the device is the presence of at least one camera and preferably two cameras in order to permit examinations on both eyes 101 of a patient 100. According to the example in FIGS. 1 and 3, two cameras 21a, 22a are used. The cameras have their lenses 21, 22 placed in holes 14a formed in a middle part of the translucent plate 10a. These cameras are positioned such that their lenses are in front of the eyes 101 of most patients, so as to be able to film them or photograph them.

The cameras are miniature cameras, for example cameras with ¼ CCD sensors with a resolution of 1920×1080, the lenses of which are compatible with holes 14a measuring from 10 mm to 15 mm.

Figure 3:
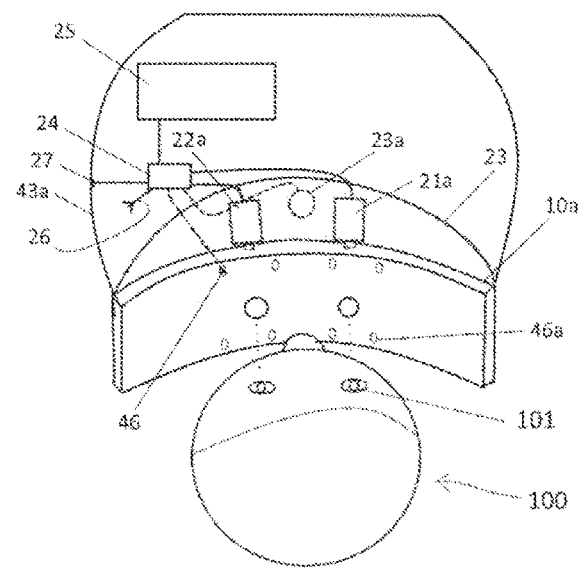
FIG. 3 is a schematic view of part of the device of the present disclosure.

The device is autonomous and the housing shown schematically in FIG. 3 comprises for this purpose at least one electronic board with microprocessor 24. This board comprises, according to the example:
- means for controlling the lighting means 23, 46 and the cameras 21, 22,
- means of acquiring video or photographic data coming from the cameras,
- calculation means suitable for carrying out computer processing of the acquired video or photographic data,
- a touch screen 25 integrated into the device and connected to the electronic board in order to allow an operator to control the device and display results of ophthalmic measurements obtained from the computer processing of data from the cameras produced by the electronic board.

The electronic board with microprocessor 24 comprises in a known manner a processor, random access memory, permanent storage memory with a storage part of a device management program, a storage part of a measurement program, and storage part for patient measurement data.

The measurement programs integrated into the electronic board are programs for carrying out ophthalmic measurements using the various lighting means and the cameras in order to carry out eye examinations on the patients, such as corneal examinations, examinations of break-up of the tear film, or other examinations using the lighting means and the cameras.

According to the example, the electronic board comprises a Wi-Fi module with an antenna 26 making it possible to communicate with an appliance such as a computer tablet, for example programmed to provide a copy of the information present on the screen 25. The board further comprises a computer port 27 such as a USB port which makes it possible, for example, to save measurements on a remote computer system or to update the program(s) on the board 24.

In the helmet configuration, the housing can operate using an on-board battery, and, in the frame-mounted configuration, the housing can be connected to an external power supply.

Figure 4:
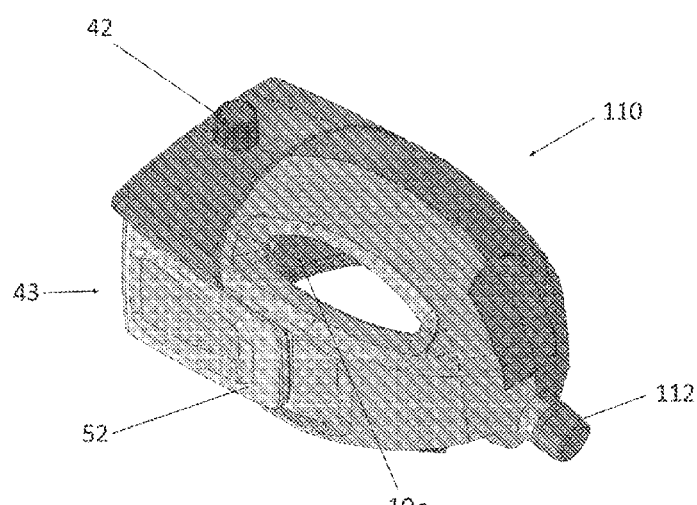
FIG. 4 shows a perspective view of a second embodiment of an ophthalmological measuring assembly of the present disclosure.

FIG. 4 shows a second embodiment of an ophthalmological measurement assembly of the present disclosure. According to this embodiment, the ophthalmological measuring device 43 is fixed to a helmet 110 intended to cover the head of the patient, which affords better monitoring of the eyes of the patient by the cameras. The helmet has a thumbwheel 112 actuating a tightening mechanism for the patient's head. The ophthalmological device is fixed to the helmet by fastening means 51 located under an upper cover 43b of the housing, these means comprising tabs 51a that fit into complementary grooves of the helmet in order to secure the device to the helmet.

Like the cover 43a, the cover 43b can be screwed onto the housing.

Figure 5:
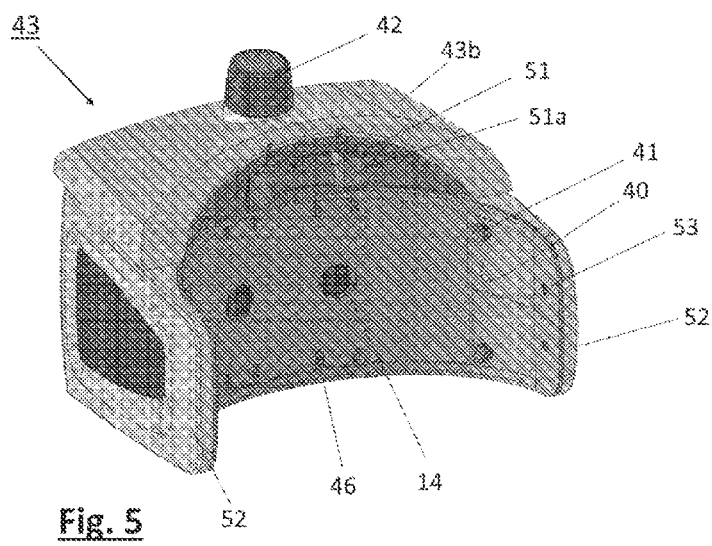
FIG. 5 shows a perspective view of an exemplary embodiment of the device of the present disclosure in relation to FIG. 4.
Figure 6:
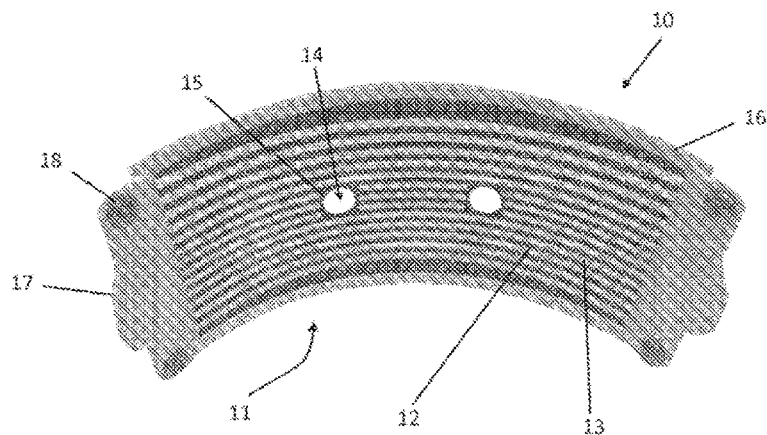
FIG. 6 shows a translucent frame carrying a test pattern that can be used in the context of an embodiment of the present disclosure.

According to FIG. 5, the device comprises means 41 for fixing a support of a complementary examination device. The support, in the example shown in FIG. 6, is a frame or a removable translucent plate 16 carrying a test pattern 10 provided with at least one hole 14 aligned with a said camera lens, said frame comprising fixing means 18 complementing the fixing means 41. The fixing means 18, 41 can be fixing means such as magnets or press-stud type fasteners. The support comprises gripping lugs 17 which allow it to be positioned and removed easily depending on the examination that is to be performed.

The ophthalmological measuring device of the present disclosure can therefore be manufactured in two configurations, a table-top configuration and a helmet configuration, on the basis of a standardized housing by using an interface plate suitable for mounting on a frame or on a helmet.

The measuring device of the present disclosure, which uses lightweight materials compatible with use on a helmet, is thus a modular device which groups together several examination systems. This device, which is the subject matter of the following claims, is not limited to the examples shown and, for example, the point light sources shown on the edge of the translucent plate can also be positioned around the through-holes of the cameras or elsewhere.

What is claimed is:

1. An ophthalmological measuring device comprising:
   an ocular measurement housing comprising a front face provided with a frame surrounding a translucent plate of a size and curvature suitable for covering the ocular field of said patient, the translucent plate having a forward facing face facing an eye or both eyes of said patient, a backlighting device for lighting the translucent plate from behind the translucent plate through an opposite face of the translucent plate opposite from the forward facing face of the translucent plate facing the eye or both eyes of said patient, at least one camera provided with a lens placed in line with a hole in the translucent plate and facing the eye or both eyes of said patient, one or more point light sources in openings on the translucent plate, for illuminating the eyes of the patient, and means for fixing one or more complementary ophthalmological measuring devices received on the translucent plate on the forward facing face of the translucent plate facing the eye or both eyes of said patient.

2. The ophthalmological measuring device as claimed in claim 1, in which the device for lighting the translucent plate from behind the translucent plate comprises an integration box diffusing the light from a white and/or near infrared light source.

3. The ophthalmological measuring device as claimed in claim 1, in which the point light sources comprise blue light emitting diodes.

4. The ophthalmological measuring device as claimed in claim 1, equipped with a complementary examination device consisting of a translucent frame carrying a test pattern provided with at least one hole aligned with a said camera lens, said frame comprising fixing means complementing the fixing means of said ophthalmological measuring device.

5. The ophthalmological measuring device as claimed in claim 1, in which the housing comprises means for fixing said measuring device to a helmet positioned on the head of a patient.

6. The ophthalmological measuring device as claimed in claim 5, in which said means for fixing said measuring device are arranged under an upper cover of the device and are intended to cooperate with complementary fixing means of the helmet.

7. The ophthalmological measuring device as claimed in claim 1, in which the housing comprises means for fixing said measuring device to an ophthalmological table frame on which the patient leans.

8. The ophthalmological measuring device as claimed in claim 7, in which the means for fixing said measuring device to said ophthalmological table frame comprise an upper cover provided with seats for receiving endings of uprights of the frame.

9. The ophthalmological measuring device as claimed in claim 1, in which the housing is a stand-alone housing which comprises at least one electronic board with microprocessor comprising means for controlling the lighting means and the cameras, means for acquiring video or photographic data coming from the cameras, and calculation means comprising one or more measurement computer programs comprising computer processing of the acquired video or photographic data, a touch screen integrated into the device in order to control the device according to the measurement program(s) and to display results of ophthalmic measurements from the computer processing carried out by the electronic board.

10. An ophthalmological measuring assembly comprising:

an ophthalmological measuring helmet, positioned on the head of a patient, and an ophthalmological measuring device having:

an ocular measurement housing comprising a front face provided with a frame surrounding a translucent plate of a size and curvature suitable for covering the ocular field of said patient, the translucent plate having a forward facing face facing an eye or both eyes of said patient, a backlighting device for lighting the translucent plate from behind the translucent plate through an opposite face of the translucent plate opposite from the forward facing face of the translucent plate facing the eye or both eyes of said patient, at least one camera provided with a lens placed in line with a hole in the translucent plate and facing the eye or both eyes of said patient, one or more point light sources in openings on the translucent plate, for illuminating the eyes of the patient, and means for fixing one or more complementary ophthalmological measuring devices received on the translucent plate on the forward facing face of the translucent plate facing the eye or both eyes of said patient.

11. An ophthalmological measuring assembly comprising:

an ophthalmological table frame; and an ophthalmological measuring device having an ocular measurement housing comprising a front face provided with a frame surrounding a translucent plate of a size and curvature suitable for covering the ocular field of said patient, the translucent plate having a forward facing face facing an eye or both eyes of said patient, a backlighting device for lighting the translucent plate from behind the translucent plate through an opposite face of the translucent plate opposite from the forward facing face of the translucent plate facing the eye or both eyes of said patient, at least one camera provided with a lens placed in line with a hole in the translucent plate and facing the eye or both eyes of said patient, one or more point light sources in openings on the translucent plate, for illuminating the eyes of the patient, and means for fixing one or more complementary ophthalmological measuring devices received on the translucent plate on the forward facing face of the translucent plate facing the eye or both eyes of said patient.

12. The ophthalmological measuring device as claimed in claim 10, in which the device for lighting the translucent plate from behind the translucent plate comprises an integration box diffusing the light from a white and/or near infrared light source.

13. The ophthalmological measuring device as claimed in claim 10, in which the point light sources comprise blue light emitting diodes.

14. The ophthalmological measuring device as claimed in claim 10, equipped with a complementary examination device consisting of a translucent frame carrying a test pattern provided with at least one hole aligned with a said camera lens, said frame comprising fixing means complementing the fixing means of said ophthalmological measuring device.

15. The ophthalmological measuring device as claimed in claim 10, in which the housing comprises means for fixing said measuring device to a helmet positioned on the head of a patient.

16. The ophthalmological measuring device as claimed in claim 15, in which said means for fixing said measuring device are arranged under an upper cover of the device and are intended to cooperate with complementary fixing means of the helmet.

17. The ophthalmological measuring device as claimed in claim 10, in which the housing comprises means for fixing said measuring device to an ophthalmological table frame on which the patient leans.

18. The ophthalmological measuring device as claimed in claim 17, in which the means for fixing said measuring device to said ophthalmological table frame comprise an upper cover provided with seats for receiving endings of uprights of the frame.

19. The ophthalmological measuring device as claimed in claim 10, in which the housing is a stand-alone housing which comprises at least one electronic board with microprocessor comprising means for controlling the lighting means and the cameras, means for acquiring video or photographic data coming from the cameras, and calculation means comprising one or more measurement computer programs comprising computer processing of the acquired video or photographic data, a touch screen integrated into the device in order to control the device according to the measurement program(s) and to display results of ophthalmic measurements from the computer processing carried out by the electronic board.

\* \* \* \* \*